(12) United States Patent
Schröter

(10) Patent No.: US 8,847,732 B2
(45) Date of Patent: Sep. 30, 2014

(54) BIOMETRIC SECURITY DEVICE

(75) Inventor: Klaus Schröter, Berlin (DE)

(73) Assignee: NanoIdent Technologies AG (AT)

( * ) Notice: Subject to any disclaimer, the term of this patent is extended or adjusted under 35 U.S.C. 154(b) by 373 days.

(21) Appl. No.: 12/812,344

(22) PCT Filed: Jan. 9, 2009

(86) PCT No.: PCT/AT2009/000004
§ 371 (c)(1),
(2), (4) Date: Dec. 3, 2010

(87) PCT Pub. No.: WO2009/086576
PCT Pub. Date: Jul. 16, 2009

(65) Prior Publication Data
US 2011/0102137 A1 May 5, 2011

(30) Foreign Application Priority Data
Jan. 9, 2008 (AT) .................................. A 30/2008

(51) Int. Cl.
  G05B 19/00 (2006.01)
  G06K 9/00 (2006.01)
  G07C 9/00 (2006.01)
(52) U.S. Cl.
  CPC .......... *G06K 9/0004* (2013.01); *G07C 9/00087* (2013.01)
  USPC ........ 340/5.82; 340/5.52; 340/5.53; 340/5.83
(58) Field of Classification Search
  None
  See application file for complete search history.

(56) References Cited

U.S. PATENT DOCUMENTS

| 5,787,185 | A | | 7/1998 | Clayden |
| 6,038,666 | A | * | 3/2000 | Hsu et al. .................... 713/186 |
| 6,078,265 | A | | 6/2000 | Bonder et al. |

(Continued)

FOREIGN PATENT DOCUMENTS

| DE | 10000720 | 7/2001 |
| EP | 0691822 | 1/1996 |

(Continued)

OTHER PUBLICATIONS

Linz, Nanoident AG realizes the first high-resolution organic photonic sensor, Jul. 5, 2005, pp. 1-2.*

(Continued)

*Primary Examiner* — Mohammad Ghayour
*Assistant Examiner* — Brian Wilson
(74) *Attorney, Agent, or Firm* — Lerner, David, Littenberg, Krumholz & Mentlik, LLP

(57) ABSTRACT

The invention relates to a security device (1) comprising at least one authentication device (17) and a locking device (18), which authentication device (17) comprises at least one sensor (2) and an evaluation and comparison module (10), and a communication link (21) exists between the locking device (18) and the authentication device (17), and the sensor (2) is provided in the form of a thin-film sensor for detecting biometric data or spectral properties of the skin and layers of tissue lying underneath, and the communication link (21) is designed to effect a secure, wireless transmission of a unique user code determined by the authentication device (17) and is limited in terms of its operating range to a close-up range, in particular less than 50 cm, and the locking device (18) is deactivated if the user code matches an identification code assigned to the locking device.

24 Claims, 3 Drawing Sheets

(56) References Cited

U.S. PATENT DOCUMENTS

| | | | |
|---|---|---|---|
| 6,484,260 B1 * | 11/2002 | Scott et al. | 713/186 |
| 6,799,726 B2 | 10/2004 | Stockhammer | |
| 6,850,147 B2 * | 2/2005 | Prokoski et al. | 340/5.53 |
| 7,236,616 B1 * | 6/2007 | Scott | 382/124 |
| 7,352,996 B2 * | 4/2008 | Kumar | 455/41.1 |
| 7,368,331 B2 * | 5/2008 | Hirai | 438/149 |
| 8,203,423 B2 * | 6/2012 | Ozolins | 340/5.52 |
| 2002/0140542 A1 | 10/2002 | Prokoski et al. | |
| 2003/0140232 A1 * | 7/2003 | De Lanauze | 713/186 |
| 2004/0222420 A1 | 11/2004 | Chang et al. | |
| 2005/0168340 A1 * | 8/2005 | Mosher et al. | 340/572.8 |
| 2007/0098227 A1 | 5/2007 | Takahashi | |
| 2007/0177769 A1 * | 8/2007 | Motoyama et al. | 382/115 |
| 2007/0253602 A1 * | 11/2007 | Amano | 382/115 |
| 2008/0024272 A1 * | 1/2008 | Fiske | 340/5.83 |
| 2010/0311390 A9 * | 12/2010 | Black et al. | 455/410 |

FOREIGN PATENT DOCUMENTS

| | | |
|---|---|---|
| EP | 1811452 A1 | 7/2007 |
| JP | 08271189 | 10/1996 |
| JP | 2000222556 A | 8/2000 |
| JP | 2002081242 A | 3/2002 |
| JP | 2002312324 A | 10/2002 |
| JP | 2004173827 A | 6/2004 |
| JP | 2006268871 A | 10/2006 |
| JP | 2007117397 A | 5/2007 |
| WO | 8804153 | 6/1988 |
| WO | 03021523 A1 | 3/2003 |
| WO | 2006026794 A1 | 3/2006 |

OTHER PUBLICATIONS

International Search Report, PCT/AT2009/000004, dated May 8, 2009.

* cited by examiner

BIOMETRIC SECURITY DEVICE

CROSS REFERENCE TO REALATED APPLICATIONS

The present application is a national phase entry under 35 U.S.C. 0371 of International Application No. PCT/AT2009/000004, filed Jan. 9, 2010, published in German, which claims the benefit of Austrian Patent Application No. A 30/2008, filed Jan. 9, 2008. The disclosures of said applications are incorporated by reference herein.

The invention relates to a security device for protecting a technical device against unauthorized use or against unauthorized access. The security device comprises at least one authentication device and a locking device, and the authentication device comprises at least one sensor and an evaluation and comparison module, and a communication link exists between the locking device and authentication device.

Technical equipment or technical devices such as security areas, security doors, data processing systems and firearms require precautions in order to ensure that only authorized or entitled persons are able to use the device for the intended purpose and that only these persons are granted access. Since information which is confidential or critical to safety is usually managed and/or stored by means of such devices or use of the device could pose a specific risk to the user himself or to the area around him and other persons, a security device must offer a particularly high degree of reliability in terms of recognizing the authorized person unambiguously. In particular, such a security device is required to use features to identify the user which are unique and cannot be forged or manipulated or can be so but only with extreme difficulty.

Numerous methods are known from the prior art which use biometric data to identify an authorized person.

Patent specification EP 0 691 822 B1 discloses an arrangement for detecting biometric features of the back of a person's hand. To this end, the user firmly grips a handle, causing the vein and tendon structure to become clearly visible on the surface of the back of the hand. The surface of the back of the hand is recorded by an optical recording system, in particular a camera, and an imaging method is used to compute the characteristic raised areas. This characteristic pattern is stored as a reference value and is used during a subsequent verification prompt as a basis for a comparison to establish a match. Imaging methods and methods of ascertaining differences from the pattern of the back of the hand presented for authentication purposes and a reference pattern generate a differential image, in which all variances between the reference pattern and the newly presented pattern are highlighted. By obtaining the best possible match, the user can be reliably authenticated.

Patent specification WO 88/04153 also discloses a device whereby the surface structure of the back of the hand, in particular the vein structure, is used as a means of unambiguously identifying a user. The document discloses how the user places a hand in a device and a camera records the surface image of the back of the hand. Using imaging methods, the surface structure or vein structure is computed; a correlation function displays the match with a reference pattern.

Patent specification U.S. Pat. No. 6,799,726 B2 discloses a security device in the form of a wristwatch. A biometric sensor is integrated in a watch and configured to record the vein structure. The watch supplies the sensor with electrical power, processes the detected biometric raw data accordingly and transmits a biometric identification feature to an evaluation device via a wireless communication link.

The disadvantages of the methods known from the prior art reside in the fact that they are not suitable for mobile applications, or are so under certain circumstances only, because a user's hand has to be placed in a device. It is also a disadvantage if a biometric sensor is integrated in another device, for example a wristwatch. During day to day use, particularly in environmental conditions where dirt, dust and high mechanical stress can be anticipated, the biometric sensor can be easily damaged when being used for its intended purpose. If the biometric sensor is integrated in a wristwatch, it must be designed so that it can be protected to withstand environmental conditions and must also be easy to clean. If the biometric sensor is not waterproof but the wristwatch as a whole is, this will lead to additional cost and complexity because the stored biometric reference values have to be transmitted or set up again.

The objective of the invention is to propose a security device which evaluates unique biometric data and authorizes use of a device or access to a system on recognizing an authorized user. Another objective of the invention is to equip the security device with a sensor for detecting biometric data which can be manufactured easily and inexpensively and has a high resistance to environmental influences and mechanical stress. Yet another objective of the invention is to propose a security device based on a modular design so that a defective or faulty component can be easily and inexpensively replaced.

The objective of the invention is achieved due to the fact that the sensor is designed as a thin-film sensor for detecting biometric data or spectral properties of the skin and layers of tissue lying underneath, and the communication link is designed to permit a reliable, wireless transmission of a unique user code determined by the authentication device and is limited in terms of its operating range to a close-up range, in particular less than 50 cm, and the locking device is deactivated if the user code matches an identification code assigned to the locking device.

Compared with known biometric sensors, a thin-film sensor is cheaper and can be manufactured with a significantly bigger surface, thereby enabling a large area of a body part to be detected on the basis of biometric features. A thin-film sensor can also be produced by means of printing methods or by vapor deposition as well as a combination of the two methods. For example, sensors produced by a printing method have an advantage in that the specific design can be individually adapted to the intended application. The advantage of vapor deposition, on the other hand, is that materials which cannot be printed or can be so but only with great difficulty can be applied, thereby enabling especially thin layers to be produced in particular.

Since a unique user code is transmitted and because transmission is limited to a close-up range, uncovering of the user code for subsequent fraudulent use is largely prevented. Another advantage of the limited operating range is that an adjacent locking device cannot be undesirably activated.

It is also of advantage that the locking device is not deactivated unless a match is found between the user code and an identification code. The particular advantage of this is that the locking device is activated automatically if the unique assignment is lost and prevents use of or access to the locked device.

Another particularly advantageous embodiment can be obtained if the sensor is made from at least one material from the group comprising organic semiconductor materials, inorganic semiconductor materials, nano-particles. The specific advantage of these materials is that they lend themselves to printing processes or vapor deposition, making manufacture of the sensor particularly efficient and inexpensive. In particular, another advantage of the claimed sensors is that they are elastically and flexibly deformable, as a result of which the sensor can be more readily adapted to the surface of the body part without the risk of damage. An advantage of another claimed embodiment is that much less energy is needed for manufacturing purposes and the problem of disposing of the sensor is much more easily dealt with than is the case with conventional sensors, which means that they lend themselves to a disposable sensor format.

Without claiming this to be a complete list, the following are some of the materials which may be used: carbon nanotubes, PPV poly(p-phenyl-vinyl). Combinations of materials are likewise conceivable, for example as a means of combining the advantageous properties of organic and inorganic semiconductors.

With a view to ensuring secure and reliable detection of a user-specific feature, it is very much of advantage if the detected biometric data is selected from the group comprising vein structure, structure of the skin surface, tissue structure.

The fingerprint is often used as a biometric identification feature. In a preferred application of the security device in an environment with difficult environmental conditions, especially where dirt can be anticipated, it may be that the structures of the finger are too dirty to permit unambiguous recognition. This being the case, it is very much of advantage to use a biometric feature with a large surface area for identification purposes. The surface structure of the skin or the vein structure can be scanned over a larger surface area and with higher resolution, thereby enabling reliable detection of the characteristic feature even if the skin surface is dirty.

A vital aspect is that the different spectral properties of the tissue are used selectively in order to record a plurality of unique biometric features at a specific recording point. In particular, the reflection and/or transmission values for different spectral elements are evaluated.

Also of advantage is another embodiment in which the sensor comprises at least one radiation source and at least one quantum detector because this means that biometric features can be detected without having to rely on ambient light or additional external illuminating means and the spectral sensitivity of the radiation source and quantum detector can be optimally adapted to one another.

In other advantageous embodiments, illumination of the surface can be controlled so that different biometric features can be selectively detected.

In the case of one embodiment where the radiation source is designed to emit electromagnetic radiation with a wavelength in the range of 350 nm to 780 nm, the surface structure of the skin can be detected. The claimed electromagnetic radiation lies in the visible optical range and is therefore advantageously well suited to detecting surface structures of the skin.

Another advantageous embodiment can be obtained if the radiation source is designed to emit electromagnetic radiation with a wavelength in the range of 750 nm to 1.4 µm. Electromagnetic radiation of this wavelength penetrates the upper skin layers and thus enables deeper lying features to be illuminated, in particular the vein structure. Another advantage of the greater penetration depth is that any dirt which might be on the skin surface will not obstruct illumination of the deeper lying features or will do so to only a negligible degree.

In one advantageous embodiment, the radiation source may be variable, in particular from 650 nm to 1.4 µm, in which case the penetration depth of the electromagnetic radiation through the tissue can be selectively controlled. By using an appropriate spectrally selective quantum detector, therefore, it is possible to detect several biometric features with only one sensor. Another option is to detect a number of different features, each at a different depth.

If the quantum detector is provided in the form of an array of several photosensitive elements, the biometric features can be detected in auf different ways. For example, sensitivity can be increased by inter-connecting several detectors during a first detection operation when the coarse structure of the skin surface or vein structure is being detected; in another detection operation, the photosensitive elements can be inter-connected in a different way to enable detailed features to be detected at high resolution.

In one embodiment, the quantum detector may be made up of elements with a differing spectral sensitivity. The individual elements may be disposed alternately on a base layer of the sensor, and every array for detecting characteristic features is in a different wavelength range. By setting up the radiation source accordingly, therefore, it is possible to detect the surface structure of the skin and the deeper lying vein structure simultaneously.

A significant advantage can be obtained if the quantum detector is selected from the group comprising organic or inorganic photodiodes, organic or inorganic photo-transistors, photo-resistors, because the components falling within this group can be manufactured rapidly and inexpensively by a printing process or vapor deposition process and by a combination of these methods. Using electromagnetic radiation in the optical range leads to a change in at least one electrical characteristic variable of the component.

With a view to ensuring universal use as far as possible and rapid and easy servicing or replacement of the sensor, it is of advantage if the sensor is provided in the form of a film, in particular self-adhesive film. A sensor of the claimed design can therefore be easily applied to a device that can be worn on the body without the need for additional retaining means.

With a view to ensuring universal use as far as possible, it is of particular advantage if the sensor is integrated or incorporated in a device selected from the group comprising an arm-band, head covering, sweat band, neck microphone, spectacles, chest strap. Such devices are commonly used on a day to day basis and are needed and used by people because they are part of standard apparel. The fact that the sensor can be universally incorporated or integrated in this manner offers a particular advantage in that no additional or complex devices are needed to fit the sensor for detecting biometric characteristics. Such devices can also be very readily adapted to the human body, thereby resulting in a high degree of wearer comfort whilst posing hardly any restriction to movement.

If the authentication device incorporates a power supply unit, autarchic operation is advantageously possible from a power point of view. The advantage of this is that in order to supply the authentication device with power, the user does not have to carry or take with him an external power source, which means that the user's mobility and freedom of movement are not restricted.

The power supply unit may be provided in the form of an electro-chemical element, in particular a battery or accumulator and/or a capacitive power storage, the advantage of which is that such power supply units are widely available and commonly used and thus represent a cost-effective option for the power supply unit.

In one advantageous embodiment, the power supply unit could be provided in the form of a chemical element which, having been activated once, emits electrical power for a period of time base on the technology used. The sensor is therefore switched on by an activation action and then detects biometric data for the time during which the power supply unit supplies power, and at the end of the operating time it can be disposed of and replaced by a new sensor. Particularly as regards the risk of the sensor becoming dirty, this embodiment offers an advantage because the sensor used always operates at optimal capacity and reliably detects the biometric data. Since the sensor proposed by the invention may be of a design with particularly low power consumption, a capacitive power storage or a two-layer capacitor will suffice to supply the sensor with electrical power.

A particularly advantageous embodiment can be obtained if the power supply unit is provided in the form of a solar cell, in particular an organic solar cell. A solar cell offers autarchic operation of the sensor for a long period of time.

An organic solar cell has another specific advantage in that it is mechanically flexible and therefore enables a sensor to be designed so that it can be readily adapted to the surface of the body part. Also of advantage is the fact that organic solar cells can be produced inexpensively and do not cause problems as far as disposal is concerned, which is a major advantage if opting for disposable sensors.

In particular, the power supply unit is designed supply power to the electromagnetic radiation source during the measuring operation. Since this measuring operation is preferably run on a periodic basis and does not take much time depending on the circumstances, the power supply unit merely needs to be designed so that it can supply the authentication device with power, in particular the electromagnetic radiation source, during the measuring operation. During periods between measurements, the power supply unit can be charged by an external source, and this is possible if using a solar cell. However, it would also be conceivable for the user to carry a power source with a high capacity with him and it charges the power supply unit by means of a near-field transmission via the user's skin during measuring pauses. These embodiments have a decisive advantage in particular because the authentication device can be built to a particularly compact design.

Biometric data can be detected at several points of the human body but there is one embodiment which is of advantage where the sensor is disposed in the region of the hand or the part of the lower arm facing the hand because very characteristic surface structures can be detected in this area and there is a high density of veins. Accordingly, even a sensor covering a small surface area can detect a large number of characteristic features and a reliable identification feature is determined.

The security device proposed by the invention is not restricted to one where the sensor is disposed in this area because in combination with another advantageous embodiment, the sensor may be disposed anywhere where characteristic biometric data can be detected. Non-restrictive examples of possible areas for fitting are the lower arm or upper arm, the region of the head and also in the region of the upper body.

An embodiment where the sensor is disposed in the region of the ankle offers an advantage because in this region, the sensor is well protected against mechanical stress and dirt by clothing. Another major advantage is that placing the sensor in this area hardly restricts the wearer's freedom of movement and it is well concealed by items of clothing.

A particularly advantageous embodiment can be obtained if the sensor is deformable and elastically reboundable because this means that it can be readily adapted to the surface to be detected without the sensor being damaged due to deformation. This embodiment is of particular advantage if the sensor is applied to a body part which continually bends or deforms as the body moves. Since the sensor can be readily adapted to the surface in this case, the risk of incorrectly detected biometric data and hence the risk of incorrect resolution or locking of the security device is significantly reduced.

The skilled person will be aware that the elastically reboundable deformations must remain within the limits specific to the material, in other words a pronounced deformation must not lead to irreversible damage to the material.

A particularly advantageous embodiment can be obtained if the sensor is designed to detect vital signals. In addition to providing a unique identification of the wearer, it is also possible to determine vital signs that are important to life. Only a living person can be authenticated and any attempts to bypass the system by presenting subsequently produced biometric features are therefore reliably thwarted.

In one embodiment, the detected vital signals may also be used to warn the wearer against a life-threatening state. Another embodiment would also be conceivable where the detected vital signals are transmitted to a control center where they can be monitored and analyzed.

In order to obtain a compact design of the security device, it is of advantage if the evaluation and comparison module and the sensor are integrated. The advantage of a claimed authentication device is that it can be integrated particularly well and can be well protected against environmental influences. In particular, given the technical options of known integration methods, especially compact and robust devices or modules can be obtained. Another advantage is that a claimed authentication device detects and evaluates the biometric data and a unique user code is issued as a result of this operation.

In one advantageous embodiment, the evaluation and comparison module is an organic semi-conductor component, which means that the advantages of organic semiconductors can be incorporated in the authentication device, in particular with a view to making disposable items.

Also claimed in particular is an embodiment where an organic semiconductor sensor is printed and inorganic semiconductor components are bonded on. However, other combinations of organic and inorganic semiconductor components may be incorporated in the claimed embodiment.

In order to run the evaluation and comparison operations, it is of advantage if the evaluation and comparison module has a memory because the detected biometric data and intermediate results of the evaluation and comparison operation can be stored in it.

An especially advantageous embodiment can be obtained if biometric reference data is stored in the memory. In order to run the authentication, detected biometric data must be compared with reference data uniquely characterizing the user. If this reference data is stored directly in the memory of the evaluation and comparison module, this will offer a significant advantage with regard to the reliability of the authentication. Every communication link for transmitting detected biometric data or reference data poses a risk in that the transmission can be disrupted or distorted. The claimed embodiment therefore offers a decisive advantage in that there is no weak point which might be critical to security from detection of the biometric data through to evaluation and comparison with reference data.

Since the position of the sensor may vary slightly due to body stance and/or movement and the detected biometric data may therefore also vary slightly, a plurality of reference data sets is stored in the memory. By comparing the detected biometric data with several sets of stored reference data, the user can therefore be authenticated more securely and reliably and the risk of incorrect resolution or locking of the security device is advantageously reduced.

Depending on the required security function of the security device, it is of advantage if the evaluation and comparison module detects biometric data of the skin continuously and/or intermittently. To ensure that highly sensitive areas or devices are secure, for example firearms or data processing facilities, it is desirable to run an authentication frequently, whereas if authentication is run as a means of controlling access, a less frequent repeat rate will suffice.

In one embodiment, the authentication may also be initiated by an activation routine. For example, the authentication device may be provided with an operating element by means of which the authentication operation is initiated. The locking device may likewise be equipped with a remote element so that the authentication operation is initiated as the authentication device is moved closer to the locking device.

In order to run complex authentication computations, it is of advantage if the evaluation and comparison module has a computer unit.

Advantageous embodiments can be obtained if the computer unit is programmed to evaluate the biometric data contained in the sensor or if the computer unit is programmed to compare the evaluated biometric data with the reference values stored in the memory.

These advantageous embodiments make for a particularly compact design of the authentication device because all the processes for detecting and evaluating biometric data are run by the evaluation and comparison module.

In another embodiment, the evaluation and comparison module can be programmed to improve or extend the reference data stored in the memory continuously in order to further enhance recognition reliability. In particular, this enables recognition reliability to be improved if the sensor is not positioned exactly. Once the wearer has been authenticated, the biometric feature can be detected at pre-definable time intervals and compared with the reference data. If an unambiguous match is not found, the newly detected biometric feature is stored in the memory as an additional reference.

In order to ensure that authentication of the user is as secure as possible, it is of advantage if the authentication unit is programmed to issue a unique user code on a continuous and/or intermittent basis. Since this user code has to be transmitted from the authentication device to the locking device which thus represents a weak point in security terms, it is very much of advantage if the user code is such that it reliably prevents falsification or manipulation. For example, the user code may be set up using an encryption method based on a one-off code. As mentioned above, different security requirements may demand continuous or intermittent authentication.

Since the communication link represents a point of attack for attempts at manipulation or falsification, it is of advantage if the data transmitted across it is secured in such a way that falsification or manipulation of the data can be prevented as far as possible and/or any fraudulent operation of the locking device can be reliably detected. In particular, this means that a transmission that is recorded with fraudulent intent will be recognized as being an instance of fraudulent use when transmitted again and rejected.

To enable the authentication device to be used for as long a time as possible, it is of advantage if it has a power-saving mode during which power consumption is less than 500 $\mu W$. Precisely in the case of devices with an autarchic power supply, it is of crucial importance for the device to consume power in the active mode only, in other words when running an authentication, and to consume as little power as possible during the rest of the time.

It is of particular advantage if the authentication device is used only periodically to run the measurements in an active operating mode and remains in a power-saving mode during the rest of the operating time, which will significantly extend the operating time.

Power consumption operated on this basis is of particular advantage as regards exposing the human body to electromagnetic fields. Since in the case of one advantageous embodiment, the power storage of the authentication unit is recharged during pauses between measurements, it is of particular advantage if the consumption of the authentication unit is low as claimed because sufficient power can be transferred to the power storage of the authentication unit by the communication link established by the skin without posing any risk to the person. In this connection, the International Radiation Protection Association (IRPA) has set threshold values for field intensities to which the human body may be exposed. In particular, a threshold value of 80 mW/kg was set for the Specific Absorption Rate (SAR) and a threshold value of 250 $mA/m^2$ (rms) for the current density (S).

Due to the claimed low power consumption of the authentication unit, the power supply unit of the authentication unit is supplied with electrical power at a level that is safe for the human organism but still adequate for the intended purpose.

To ensure reliable authentication, it is of advantage if the authentication device has a wireless position sorting system. For example, this might be provided in the form of GPS or dGPS, or any other wireless position sorting system could be used as an alternative. In an area with several devices which require authentication, the authentication device may selectively initiate authentication with a special device by recognizing the current position. For example, it is possible for the wearer to move in a set area, having been authenticated once, without losing the assigned authority.

In one embodiment, however, it would also be conceivable for the position of the authentication device to be continuously monitored, in order to keep a log of movements or to issue a warning report on leaving and/or approaching an area.

In addition to the communication link between the authentication device and the locking device, the authentication device may also be provided with a network communication module. This network communication module may be used to establish a communication link with a data exchange point. The detected biometric data can therefore be transmitted across this preferably wireless communication link to an administration or monitoring unit.

Based on another advantageous embodiment, detected vital signals can also be transmitted across this communication link to an administration or monitoring unit.

A particularly advantageous embodiment can be obtained if the authentication device has a closure element, which is programmed to emit a trigger signal. When the authentication device is fitted on the body part, it is positively or non-positively secured by activating and locking the closure element. Activation or locking also causes the authentication operation to be initiated.

With a view to saving energy, it is of decisive advantage if the detection of the biometric features is not run on a continuous basis. The triggering action indicates that the wearer has positioned the authentication device, in particular the sensor, over the biometric feature to be detected. The biometric feature is then unambiguously detected and having been unambiguously recognized, the assignment to the locking device is initiated. As long as the closure element is activated and locked, the biometric feature does not need to be detected continuously and it is sufficient to opt for periodic detection, for example. However, it would also be possible for the authentication to remain valid until the authentication unit is removed, in which case no further detection is necessary.

To provide additional protection against misuse, the authentication device has an authenticity feature. For example, the data detected by the sensor detected could be recorded and presented to the evaluation and comparison module for evaluation in order to in order to flag a fraudulent assignment to a locking device. The authenticity feature is preferably configured so that every manipulation of the authentication device can be unambiguously recognized, for example so that it can be destroyed and not reproduced after a manipulation.

In one advantageous embodiment, the authenticity feature may also be configured so that a manipulation of the authentication device will cause the evaluation and comparison module to be destroyed and, in one advantageous embodiment, the reference data stored in the memory in particular.

Another feature to provide unique authentication of a wearer can be obtained if the authentication device has a length measuring device. The authentication device is positively or non-positively arranged on a body area and such that it sits round a circumference, as is the case. The measurement of the enclosed length may be used as another feature by which a wearer can be uniquely authenticated. The length measuring device may be any device suitable for determining the distance between two points or a change in the distance and can be integrated in or on an authentication device.

For example, the length measuring device might be a resistively acting measuring tape, whereby a change in length will cause a change in overall resistance.

Since the operating range of the communication link is limited to the close-up range, a whole range of different technologies and communication modules is available for producing the communication link, for example Bluetooth, RFID, IrDA. These communication technologies are widely used, standardized and therefore usually inexpensive. The requisite additional components are also widely available and inexpensive.

A very decisive advantage can be obtained if the communication link is based on the near-field of the user's skin In the case of such a communication link, any influence or manipulation by third parties is largely prevented because the communication link requires physical contact between the locking device and user's skin, for example by gripping the device to be secured. This physical contact may be used to keep the secured device unlocked as long as the device is still in contact with the user. In the situation of securing firearms, for example, this would have an advantage in that these would also be or remain locked if the user were to remain in the close-up range of the locking device, for example if the weapon were appropriated by a third party.

In one advantageous embodiment, the communication link may be established by means of the skin for a contactless transmission. In this case, an electric field is generated on the skin which can be used in a close-up range of up 50 cm as a communication link, for example. The presence of the user in the close-up range of the locking device is therefore sufficient to permit an assignment.

A very advantageous embodiment can be obtained if the operating range of the communication link can be adjusted because this will make it possible to ascertain unambiguously at what distance between the locking device and authentication device an unambiguous assignment can be made between these two devices. In particular, it is possible to ascertain unambiguously from what distance the assignment is no longer valid. In one advantageous embodiment, for example, it might be necessary, in order to set up an assignment, for the authentication device to be disposed in the immediate close-up range of the locking device. Once the assignment has been made, the user can then move within a range around the locking device without losing the assignment.

Another option is to run recognition on the basis of proximity, for example, in which case the authentication is run automatically on approaching the locking device.

With a view to securing the transmitted user code, it is also of advantage if the authentication and locking device has an encryption and/or decryption unit. In this claimed embodiment, the transmitted data and if necessary other communication security routines are protected, for example by one-off codes or public key systems, so that even if the communication is fraudulently recorded, it will be impossible or very difficult to work back to the contents of the communication.

The transmitted user code is checked in the locking device and in the event of a match with an identification code, the locking device is assigned to the authentication device for a limited period of time. The advantage of this claimed embodiment is that once established, an assignment is automatically deleted again and a new authentication is needed in order to gain access to the secured device again. This embodiment therefore advantageously ensures that a device is not left unlocked unintentionally and unsupervised and hence exposed to manipulation by third parties. When a user sets up an assignment to a secured device and then moves away from it, in particular out of the operating range of the communication link, the latter would automatically lock after a predefinable time and thus prevent manipulation by third parties.

In one advantageous embodiment, the locking device may be configured so that the user is alerted to the fact that the assignment is about to be lost and can therefore initiate another authentication, for example. In another embodiment, the locking device may be configured so that the authentication device prompts a new authentication by means of a remote control means or across the communication link.

Once an assignment has been set up, the user is able to enter settings from the authorized device and adapt it to his requirements. To prevent these changes or modifications from being mistakenly lost, it is of advantage if, when an assignment is active, it is not possible to make an assignment to another authentication device. An authenticated, authorized device can therefore only be used by one user at a time. The assigned user muss must therefore actively cancel the assignment in order to release the device for another user.

The advantage of a locking device comprising a locking element and a drive means is that when an assignment has not been set up, an unambiguous non-operating position of the locking element exists. The locking device is preferably designed so that the locking device is inactive in the non-operating state, in other words the device is locked, which means that entry or access is not permitted and the device cannot be used. This is a major advantage because fraudulent use or deployment by selective manipulation of the locking device is prevented. For example, this means that it is not possible to maliciously establish a permanently unsecured state by cutting the power supply to an authorized locking device.

The lock element is preferably provided in the form of a lock bolt, although any lock elements which will permit mechanical locking or fixing may be used. The drive means may be provided in the form of an actuator, although all devices suitable for moving a lock element would be conceivable.

In one embodiment, the locking device may also be provided in the form of electronic or data-controlled locking elements, for example log-on masks, which do not permit access until successfully authenticated.

In another advantageous embodiment, the drive means of the locking device is designed to move the lock element between a locked and an unlocked position. A displaceable lock element offers a decisive advantage in that it is well suited to providing protection against manipulation and fraudulent operation. In particular, it may be disposed in a device to be secured so that it is out of reach from outside. Following a successful authentication, the lock element is moved from the locked into the unlocked position so that the secured device is released and access permitted.

As part of developments made to firearms, in particular hand guns, the mechanical firing operation has been very much fine-tuned. Based on one embodiment, therefore, the locking device is provided in the form of an electronic firing system, the particular advantage of which is that extraordinarily high firing repeat rates can be obtained because no or hardly any moved parts are needed for the firing operation. This high firing speed accompanied by a significant increase in security in terms of access by authorized persons are the specific advantages obtained as a result of this claimed embodiment. Also of advantage is the fact that the locking device can be made to a significantly more compact design because many of the components needed in the past are unnecessary, resulting in a particular advantage with respect to reliability.

In one advantageous embodiment, the locking device could also be designed so that any attempt at misuse by unauthorized persons triggers a protection mechanism. This could render the locking device unusable, for example, or give the unauthorized person a painful warning, for example an electric shock.

A significant gain in security can be obtained if the locking device has a status display. For the user of a security device proposed by the invention, it is of advantage if the locked status of the locking device can be clearly, quickly and unambiguously seen. Taking a hand gun as an example, this claimed option could be obtained using a lamp device on the handle end, which emits a strong, directed light beam. This light beam may be used as a sighting aid for example, in which case it is active when the locking device is deactivated. In the event of unauthorized use, a weapon could be aimed at the authorized user for example, in which case he will be able to tell immediately from this feature whether the locking device is active or deactivated and can then take the necessary steps to defend himself.

The invention will be explained in more detail below with reference to examples of embodiments illustrated in the appended drawings.

These illustrate schematically simplified diagrams as follows.

Figure 1:
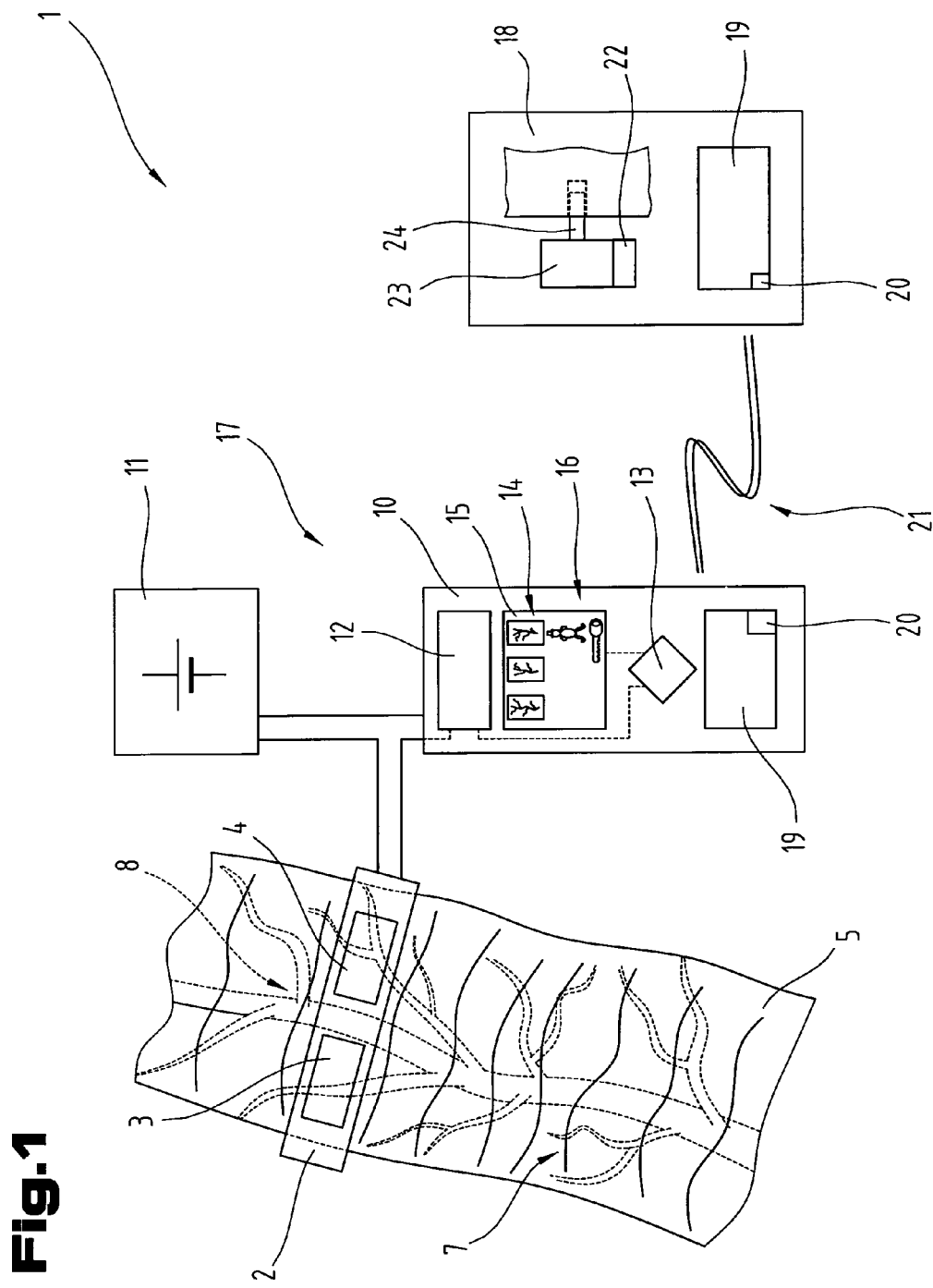
FIG. 1 is a block diagram illustrating the security device proposed by the invention.

FIG. 3 a) and b) show a front and rear view of one possible embodiment of the authentication device;

FIG. 4 a) and b) show a front and rear view of another possible embodiment of the authentication device.

Firstly, it should be pointed out that the same parts described in the different embodiments are denoted by the same reference numbers and the same component names and the disclosures made throughout the description can be transposed in terms of meaning to same parts bearing the same reference numbers or same component names. Furthermore, the positions chosen for the purposes of the description, such as top, bottom, side, etc., relate to the drawing specifically being described and can be transposed in terms of meaning to a new position when another position is being described. Individual features or combinations of features from the different embodiments illustrated and described may be construed as independent inventive solutions or solutions proposed by the invention in their own right.

All the figures relating to ranges of values in the description should be construed as meaning that they include any and all part-ranges, in which case, for example, the range of 1 to 10 should be understood as including all part-ranges starting from the lower limit of 1 to the upper limit of 10, i.e. all part-ranges starting with a lower limit of 1 or more and ending with an upper limit of 10 or less, e.g. 1 to 1.7, or 3.2 to 8.1 or 5.5 to 10.

FIG. 1 is a block diagram illustrating the security device 1 proposed by the invention. A sensor 2 comprising a source 3 of electromagnetic radiation and a quantum detector 4 is placed over a body part 5. The sensor 2 is preferably placed on those areas of body parts in which a plurality of characteristic biometric data is present. For example, in the area of the lower arm 6, a characteristic structure of the skin surface 7 and/or a characteristic vein structure 8 can be detected.

The sensor 2 and the evaluation and comparison module 10 are supplied with electrical power from a power supply unit 11 and, if necessary, two separate power supply units may be provided in order to supply the sensor 2 and the evaluation and comparison module 10. The biometric data detected by the sensor is transmitted to the evaluation and comparison module 10 and evaluated by the computer unit 12. The evaluated biometric data is compared with biometric reference data 14 stored in the memory 15 by a comparison module 13. If a match is found, a unique, unambiguous user code is generated from the stored personal data 16.

The authentication device 17 and the locking device 18 each have a communication module 19 which may additionally incorporate an encryption and/or decryption module 20 if necessary. The communication module 19 is programmed to establish a wireless close-up range communication link 21 between the authentication device 17, in particular the evaluation and comparison module 10, and the locking device 18. The locking device 18 also has an evaluation module 22, which compares the unique and unambiguous user code transmitted across the communication link 21 with an identification code assigned to the locking device and in the event of a match activates a drive means 23 so that it moves a lock element 24 from a locked into an unlocked position.

When detecting biometric data, in particular when continuously or periodically detecting, the sensor 2 must be such that it can be adapted as well as possible to the surface shape of the body part in order for the biometric data of the skin surface structure 7 or vein structure 8 to be clearly detected. The main advantage of a thin-film sensor as proposed by the invention resides in the fact that it is can be flexibly deformed and is elastically reboundable, thereby resulting in good adaptation to the surface shape of the area of a body part. In one advantageous embodiment, the sensor 2, in particular the source 3 and quantum detector 4, are made from organic semiconductors material, enabling the sensor to be manufactured particularly inexpensively, in particular in the form of so-called disposable sensors. Especially if the sensor is to be used in difficult environmental conditions or if a large amount of dirt can be anticipated, it is of particular advantage if the sensor for detecting biometric data can be disposed of without causing problems for the environment after being used once and replaced by a new inexpensive sensor.

Depending on the biometric feature to be detected, the source 3 emits electromagnetic radiation with a specific wavelength. In order to detect skin surface structures 7, the skin is illuminated in the optical visible range, in which case the wavelength range of 650 nm to 780 nm in particular will suffice. However, if detecting the vein structure 8 lying deeper in the skin, it will be necessary to illuminate with electromagnetic radiation of a longer wavelength, in particular in the range of from 750 nm to 1.4 μm, because it will be able to penetrate the skin more deeply and thus illuminate the deeper lying vein structures. The quantum detector 4 is preferably provided in the form of a plurality of photosensitive elements, which may be arranged in a chessboard pattern for example, the size of the first photosensitive elements determining the maximum resolution capacity which can be achieved. The source 3 may optionally also be provided in the form of a plurality of individual elements emitting electromagnetic radiation, which may be integrated in an alternating arrangement with detector elements. The advantage of this arrangement resides in the fact that uniform illumination of the area to be detected can be achieved due to the way the lamp elements are distributed. Other possible ways of arranging the source and detectors will be described in connection with FIG. 3.

In order to supply the sensor 2 with electrical power, the power source 11 is preferably disposed on the sensor 2 and is provided in the form of a chemical element. In one advantageous embodiment, however, this power source 11 could also be provided in the form of a solar cell, in particular an organic solar cell. In another embodiment, the chemical element might be a disposable one. This being the case, the chemical element is activated by an activation means and supplies electrical power for a period of time depending on the technology used. With a view to producing a disposable sensor, an embodiment of this type is of particular advantage.

In one embodiment, the power source 11 may also be disposed together with the evaluation and comparison module 10 on the sensor 2, thereby advantageously resulting in a very compact and highly integrated authentication device 17.

Several sets of biometric reference data 14 are preferably stored in the memory 15 of the evaluation and comparison module 10. Since the detected biometric might vary slightly due to different positions of the sensor and varying contact pressure, it is of advantage if the comparison module 13 contains a plurality of sets of biometric reference data 14 as comparison options. This reference data is determining during a learning process, for example, where the sensor 2 is positioned in the detection area and a reference pattern is recorded for a slightly different position or slightly different contact pressure.

A personal data set 16 may also be stored in the evaluation and comparison module 10, in particular in the memory 15. If a match is found between the detected biometric features and the stored reference data, a unique, unambiguous user identification is generate from the personal data set, in particular a user code. This user code is such that unambiguous authentication is possible on the one hand and forgery or manipulation of the code is prevented on the other hand. Since a preferably wireless communication link 21 exists between the authentication device 17 and the locking device 18, the transmitted user code could be recorded by third parties and then used with malicious intent to set up an assignment to the locking device 18. However, the special properties of the code ensure that an unauthorized assignment by third parties is reliably prevented.

The communication link 21 is preferably provided in the form of a communication link operating in the close-up range and by known technology such as Bluetooth, IrDA, RFID. Since wireless communication links are accessible to third parties and there is therefore a possibility of falsification or interference by third parties, the transmitted data could additionally be encrypted by an encryption and/or decryption module so that even if the transmitted data were fraudulently recorded and analyzed, it would not be possible to work backwards to the contents of the transmitted information. This encryption may be operated on the basis of a one-off code or so-called public key systems.

More particularly preferred is an embodiment of the communication link 21 in the form of a near-field communication established via the user's skin The advantage of an embodiment of this type is that the person must remain within a specific range around the locking device or must be in contact with it. This offers particularly good protection against interference to the transmission by third parties because the range of the transmission can be effectively limited by an appropriate choice of transmission parameters.

The locking device 18 is designed so that, in a non-operating position, in other words when there is no active assignment to an authenticated user or the assignment has been lost, the lock element 24 is disposed in a locked position. The function of the evaluation module 22 is to analyze the transmitted user code and if a match with an identification code is found activate the drive means 23 so that the lock element 24 is moved into an unlocked position. The authorization information and identification codes may be stored in the evaluation module 22, for example, and specify which user codes may set up an assignment to the locking device.

Figure 2:
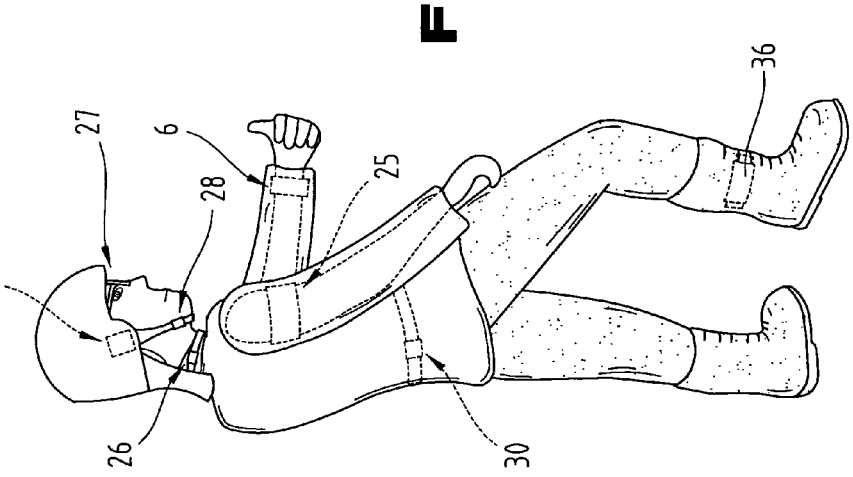
FIG. 2 illustrates possible positions on the human body where the sensor can be fitted for detecting biometric data.

FIG. 2 illustrates possible positions for fitting the sensor or authentication device. The advantage of fitting it on the lower arm 6 is that a high vein density with different structures and a plurality of different skin surface structures can be detected in this area. In this position, however, there is a risk of greater mechanical stress and more likelihood of exposure to dirt and dust.

There is an advantage to fitting on the upper arm 25 because there is likely to be less mechanical stress and less risk of dirt.

Also of advantage are arrangements where the sensor and/or authentication device is disposed in the region of a person's head. For example, one option is to dispose it in or on a neck microphone 26 or the frame of a pair of goggles 27. If the user is wearing a head covering, for example a helmet or a cap, an arrangement on the retaining strap 28 or the internal face of the head covering 29 is possible. Another option is to dispose the sensor or authentication device on a belt 30, in which case this belt might be worn as a chest strap for example.

This list of possible fitting positions should not be seen as restrictive and, in particular, the sensor or authentication device may be placed on all areas of the human body where characteristic biometric data can be detected.

Figure 3A:
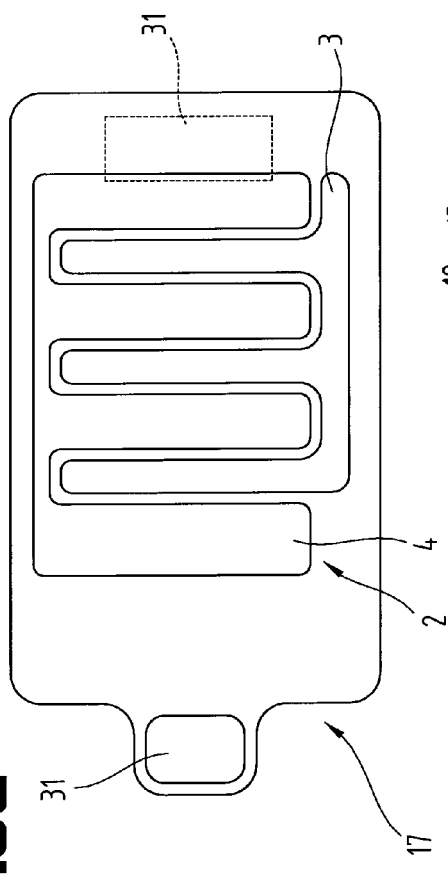
Figure 3B:
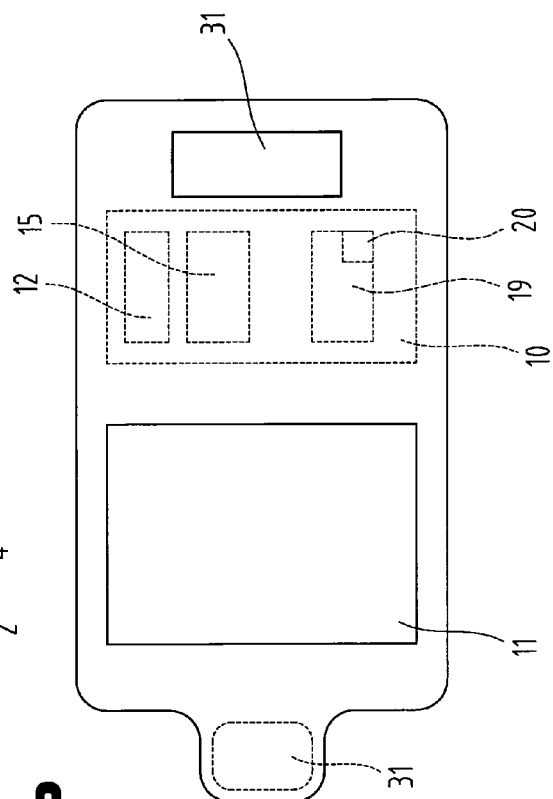

FIGS. 3a and 3b illustrate an example of an embodiment of an authentication device 17. FIG. 3a shows a view onto the sensor 2 and this face is usually placed in contact with the skin surface.

In the embodiment illustrated here, the authentication device 17 is provided in the form of a cuff, which can be fitted flexibly around a body part, for example an arm. The cuff is secured around the body part by means of the closure element 31. FIG. 3a illustrates another example of an arrangement of the sensor 2, in particular the source 3 of electromagnetic radiation and the quantum detector 4. They are nested one in the other in a finger pattern in which one finger of the radiation source 3 illuminates the adjacent area detected by the detector 4. Apart from this exemplary arrangement, all other arrangements would be conceivable which enable an area of the skin surface of a body part to be illuminated by a radiation source so that the image of the illuminated area can be recorded by a quantum detector. In particular, arrangements which offer advantages are those where the detected area is illuminated as uniformly as possible and the disposition of the radiation source effects or restricts the detector range as little as possible.

The power supply unit 11 is disposed on the second surface, as illustrated in FIG. 3b. The evaluation and comparison module 10 may optionally also be disposed there but in one advantageous embodiment it is disposed in the cuff so that it is protected. In one particularly advantageous embodiment, the power supply unit 11 may be provided in the form of an organic solar cell. The advantage of this embodiment is that the authentication device 17 can be powered on an autarchic basis. The significant advantage of organic solar cells is that they are flexible and can therefore be readily adapted to the surface shape of the body part when fitting the cuff. Organic solar cells and in particular all components made from organic semiconductor material have an additional advantage in that their disposal poses fewer problems than is the case when disposing of devices or components made from inorganic semiconductor material.

In one embodiment, the sensor and the evaluation and comparison module, in particular individual elements of them, may also be disposed separately from one another. For example, it would be conceivable for the evaluation and comparison module to be disposed on or in a piece of equipment and the detected biometric data is transmitted via a communication means, preferably a wireless, from the sensor to the evaluation and comparison module. If the sensor is damaged or becomes dirty, it is a simple and uncomplicated matter to replace it with a new one. Another conceivable embodiment is one where the memory in which the biometric reference data is stored can be connected to the evaluation and comparison module. This embodiment also has an advantage because in the event of malfunction of the authentication device, the memory containing the reference data can be uncoupled and inserted in a new authentication device. This makes it quicker and less complicated to replace a defective authentication without having to run the learning process in order to set up the biometric reference data again.

Figure 4A:
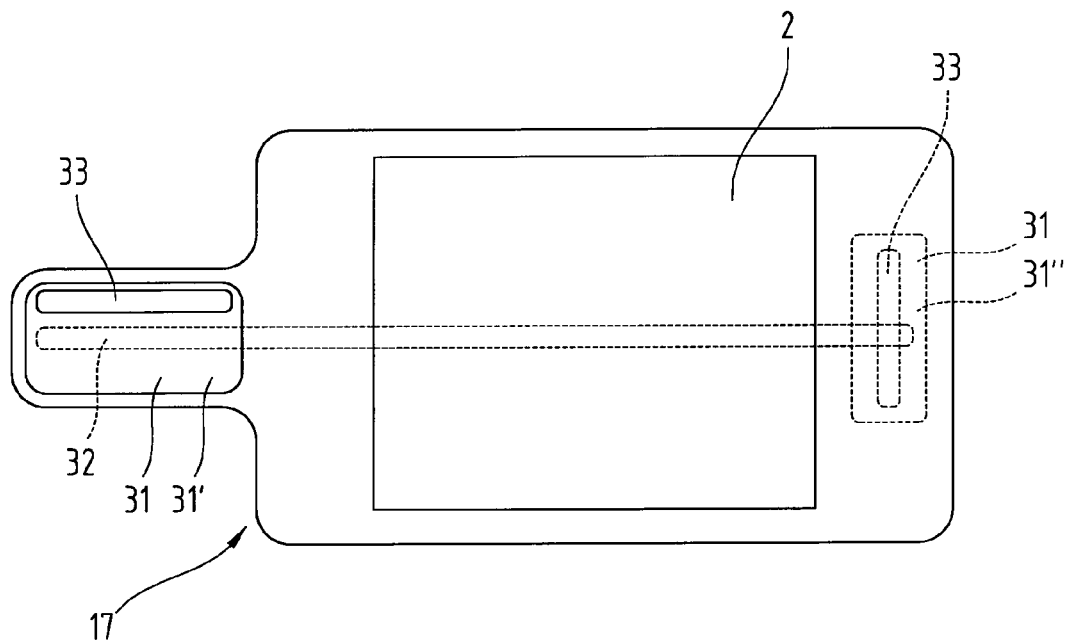
Figure 4B:
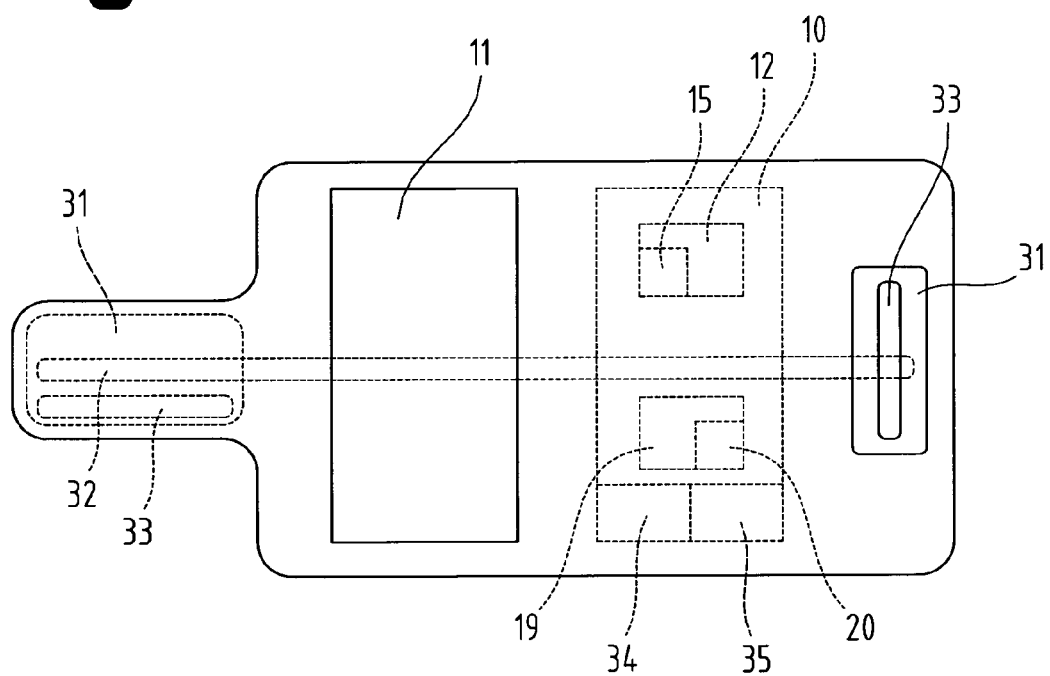

FIGS. 4a and 4b illustrate another example of an embodiment of an authentication device 17. FIG. 4a again shows the view onto the sensor 2 and this face is usually placed in contact with the skin surface. The authentication device 17 is provided in the form of a cuff which encloses a body part and is positively or non-positively secured to it by connecting the two parts 31', 31" of the closure element 31.

The closure element 31 is designed so that when the two parts 31', 31" of the closure means 31 are closed or placed in contact, a so-called trigger is generated. This trigger initiates the authentication operation and detects a biometric feature. When a match is found with reference values stored in the memory 15, the assignment to the locking device is set up, after which a unique user code is continuously and/or intermittently transmitted. As long as the closure element 31 is closed or remains in contact, it is not necessary to detect a biometric feature again. When the closure element is released, another trigger is generated, which may be used to cancel the assignment to the locking device for example. The device generating the trigger may be any type of switch or pulse transmitter which operates both on contact and without contact.

Since the detection and evaluation of biometric features requires electrical power but there is only a limited amount of space available for this on a compact authentication device, a significant amount of energy is saved using this embodiment which means that the authentication device can operate for a much longer period of time.

In order to prevent a locked or closed and successfully authenticated authentication device 17 from being used fraudulently, for example by separating the device and closing or locating the closure element 31, an authenticity feature 32 may be provided in the authentication device 17. This authenticity feature 32 is designed so that fraudulent use or manipulation of the authentication device 17 is prevented and can be recognized as such. In particular, a successful assignment to a locking device is cancelled if manipulation is detected. A preferred embodiment is one where the authenticity feature is also capable of generating a trigger signal.

Since reference data 14 which might also be used for fraudulent purposes is also stored in the memory 15 of the evaluation and comparison module 10, the authenticity feature 32 in one embodiment might be designed so that an attempt at manipulation will cause this reference data to be destroyed so that it cannot be restored.

The circumference of the body part around which the authentication device is fitted might also be regarded as a characteristic feature. The closure element 31 may incorporate a length measuring device 33, for example, which determines the enclosed circumference when the closure element 31 is closed. If the circumference matches a stored circumference, this may already suffice as an authentication if only low grade security is required. However, this match could also serve as a trigger and initiate a biometric authentication operation, for example. The length measuring device 33 may be provided in the form of a variable resistor which can be mechanically acted on or optical distance detection means could also be used. The relevant skilled person will be familiar with several compact devices and methods capable of determining a length.

A positioning unit 34 enables the position of the authentication device 17 to be set by a control and monitoring center and/or enables the authentication device to determine the position within an area automatically. The positioning unit 34 is preferably of a wireless design, for example GPS or d-GPS.

By means of a network communication module 35, preferably a wireless communication module, the authentication device 17 may exchange data with a control and/or monitoring center. In one advantageous embodiment, the sensor 2 is designed to detect vital signals, in which case the detected vital signals can be transmitted across the communication link of the network communication module 35 to the control and/or monitoring center. Accordingly, the latter is in a position to monitor the wearer's state of health at any time. In particular, it is possible to ensure that an authentication is run for only one person with vital signs at any one time.

The embodiments illustrated as examples represent possible variants of the of the security device and it should be pointed out at this stage that the invention is not specifically limited to the variants specifically illustrated, and instead the individual variants may be used in different combinations with one another and these possible variations lie within the reach of the person skilled in this technical field given the disclosed technical teaching. Accordingly, all conceivable variants which can be obtained by combining individual details of the variants described and illustrated are possible and fall within the scope of the invention.

For the sake of good order, finally, it should be pointed out that, in order to provide a clearer understanding of the structure of the security device, it and its constituent parts are illustrated to a certain extent out of scale and/or on an enlarged scale and/or on a reduced scale.

The objective underlying the independent inventive solutions may be found in the description.

Above all, the individual embodiments of the subject matter illustrated in FIGS. 1 to 4 constitute independent solutions proposed by the invention in their own right. The objectives and associated solutions proposed by the invention may be found in the detailed descriptions of these drawings.

LIST OF REFERENCE NUMBERS

1 Security device
2 Sensor
3 Source of electromagnetic radiation
4 Detector of electromagnetic radiation
5 Body part
6 Lower arm
7 Skin surface structure
8 Vein structure
10 Evaluation and comparison module
11 Power supply unit
12 Computer unit
13 Comparison module
14 Biometric reference data
15 Memory
16 Personal data set
17 Authentication device
18 Locking device
19 Communication module
20 Encryption and/or decryption module
21 Communication link
22 Evaluation module
23 Drive means
24 Lock element
25 Upper arm
26 Neck microphone
27 Goggles
28 Retaining strap
29 Head covering/helmet
30 Carrier belt
31 Closure means
32 Authenticity feature
33 Length measuring device
34 Positioning unit
35 Network communication module
36 Ankle

The invention claimed is:

1. A security device comprising at least one authentication device and a locking device, wherein the authentication device comprises a closure element configured to generate a trigger signal to initiate user authentication through detection of biometric data from a user, a sensor configured to detect the biometric data, wherein the biometric data includes a vein structure, a structure of a skin surface, and a tissue structure, the sensor including an organic semiconductor, an electromagnetic radiation source for emitting electromagnetic radiation and a quantum detector for detecting the emitted electromagnetic radiation, wherein the sensor is provided in the form of a deformable and elastically reboundable thin-film sensor and is controlled such that the vein structure, the structure of the skin surface, and the tissue structure are selectively detected, such that the electromagnetic radiation source is configured to emit the electromagnetic radiation with different wavelengths based on the selected biometric data to be detected, an evaluation and comparison module configured to compare the detected biometric data with reference biometric data, a near-field communication link established via the user's skin after comparing the detected biometric data and which exists between the locking device and the authentication device, wherein the near-field communication link is programmed to effect a secure, wireless transmission of a unique user code determined by the authentication device, and the locking device is deactivated if the unique user code matches an identification code assigned to the locking device.

2. The security device according to claim 1, wherein the radiation source emits the electromagnetic radiation with a wavelength in the range of 650 nm to 1.4 μm.

3. The security device according to claim 1, wherein the quantum detector comprises an array of several photosensitive elements.

4. The security device according to claim 3, wherein the quantum detector is selected from the group comprising organic or inorganic photodiodes, organic or inorganic phototransistors, and photo-resistors.

5. The security device according to claim 1, wherein the sensor comprises an adhesive film.

6. The security device according to claim 1, wherein the sensor is disposed in a device selected from the group comprising an armband, head covering, sweat band, neck microphone, goggles, and chest strap.

7. The security device according to claim 1, wherein the authentication device has a power supply unit.

8. The security device according to claim 7, wherein the power supply unit comprises an electro-chemical element.

9. The security device according to claim 7, wherein the power supply unit comprises a solar cell.

10. The security device according to claim 1, wherein the sensor is configured to detect vital signs.

11. The security device according to claim 1, wherein the evaluation and comparison module and the sensor are integrated.

12. The security device according to claim 1, wherein the evaluation and comparison module has a memory.

13. The security device according to claim 12, wherein the reference biometric data is stored in the memory.

14. The security device according to claim 1, wherein the biometric data is continuously and/or intermittently detected.

15. The security device according to claim 1, wherein the evaluation and comparison module has a computer unit.

16. The security device according to claim 1, wherein the authentication device is designed to transmit the unique user code continuously and/or intermittently.

17. The security device according to claim 1, wherein the authentication device has a power save operating mode, a wireless position sorting system, a network communication module, an authenticity feature, or a length measuring device.

18. The security device according to claim 1, wherein the authentication device and the locking device have an encryption and/or decryption unit.

19. The security device according to claim 1, wherein the locking device is configured to set up a data assignment to the authentication device for a limited time.

20. The security device according to claim 1, wherein the locking device is assigned to only one specific authentication device.

21. The security device according to claim 1, wherein the locking device comprises a lock element.

22. The security device according to claim 21, wherein the lock element comprises a lock bolt and drive means is designed to move the lock element between a locked and an unlocked position.

23. The security device according to claim 1, wherein the locking device comprises an electronic firing system.

24. The security device according to claim 1, wherein the locking device has a status display.

\* \* \* \* \*